United States Patent [19]

Hattori

[11] 4,264,206
[45] Apr. 28, 1981

[54] DUST PARTICLE ANALYZER

[75] Inventor: Shuzo Hattori, Nagoya, Japan

[73] Assignee: The Kimmon Electric Co., Ltd., Tokyo, Japan

[21] Appl. No.: 669

[22] Filed: Jan. 3, 1979

Related U.S. Application Data

[63] Continuation-in-part of Ser. No. 726,030, Sep. 23, 1976, abandoned.

[51] Int. Cl.³ .............................................. G01N 21/01
[52] U.S. Cl. ..................................... 356/343; 250/574
[58] Field of Search ....................... 356/337, 338–340, 356/342, 343; 250/574

[56] References Cited

U.S. PATENT DOCUMENTS

| | | | |
|---|---|---|---|
| 3,612,689 | 10/1971 | Liskowitz | 356/342 |
| 3,624,835 | 11/1971 | Wyatt | 356/343 |
| 3,850,525 | 11/1974 | Kaye | 356/73 |
| 4,053,229 | 1/1976 | McCluney | 356/338 |
| 4,110,043 | 9/1976 | Eisert | 356/337 |

OTHER PUBLICATIONS

Barrett, J. J. and N. I. Adams, III "Laser-Excited Rotation-Vibration Raman Scattering in Ultra-Small Gas Sampler", Josa, vol. 58, No. 3, p. 311, 3/68.

Primary Examiner—John K. Corbin
Assistant Examiner—Bruce Y. Arnold
Attorney, Agent, or Firm—Richard J. Birch

[57] ABSTRACT

This invention provides a dust particle analyzer comprising:

A laser producing a light beam polarized in a first plane including said light beam;

Means to convert said light beam into a cone light beam of a first small angle;

Means to convey a volume of sample air containing dust particles under surveillance onto a highly illuminated region at the apex of said cone light beam;

Means to collect light beams scattered forward from said dust particles in a first solid angle surrounded by the inner cone of a second small angle larger than said first small angle and the outer cone of a third small angle, the cosine of which is substantially equal to unity;

Means to collect light beams scattered backward from said dust particle in a second solid angle surrounded by the inner cone of said second small angle and the outer cone of said third small angle;

Means to produce a first signal which is proportional to the component of said forward scattered light beams polarized in said first plane and in said first solid angle;

Means to produce a second signal which is proportional to the component of said scattered light beams polarized in said first plane and in said second solid angle; and Means to count the number of dust particles contained in a volume of said sample air and belonging to the respective groups defined according to the refractive index and the diameter of dust particles determined by said first and second signals.

6 Claims, 12 Drawing Figures

F I G. 3B
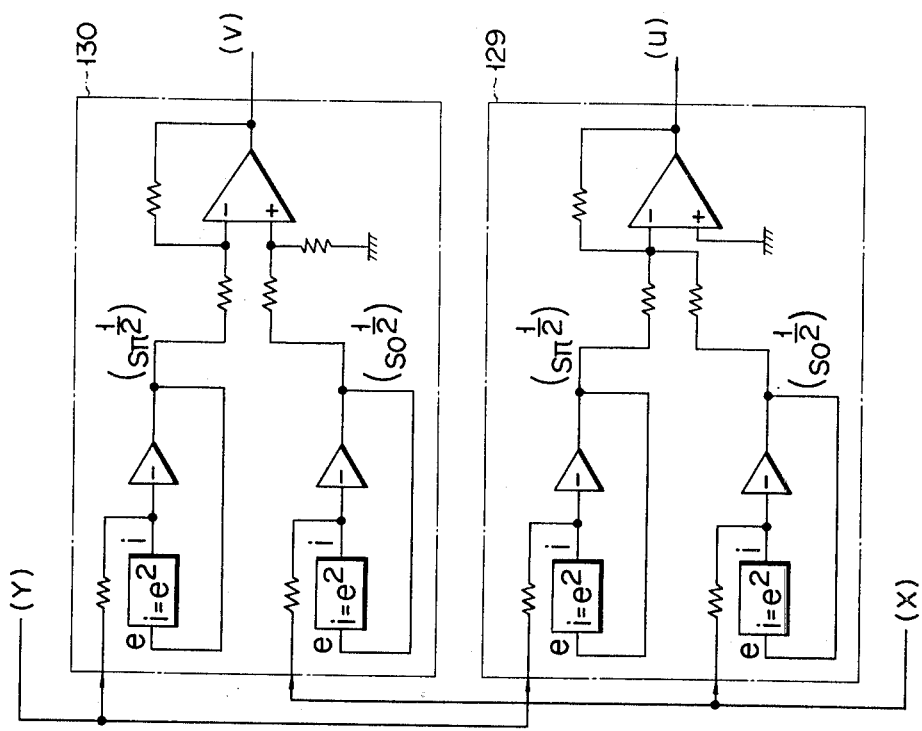
F I G. 3A
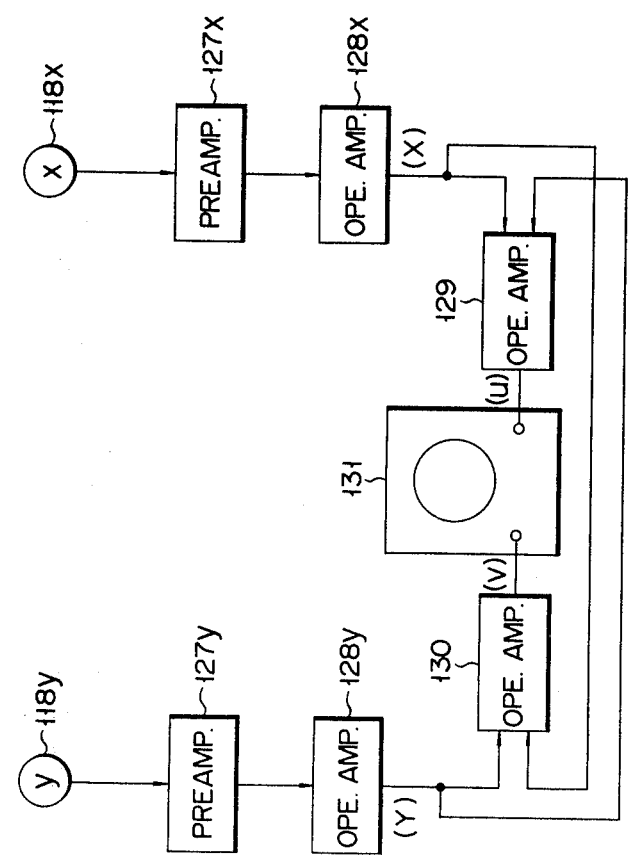

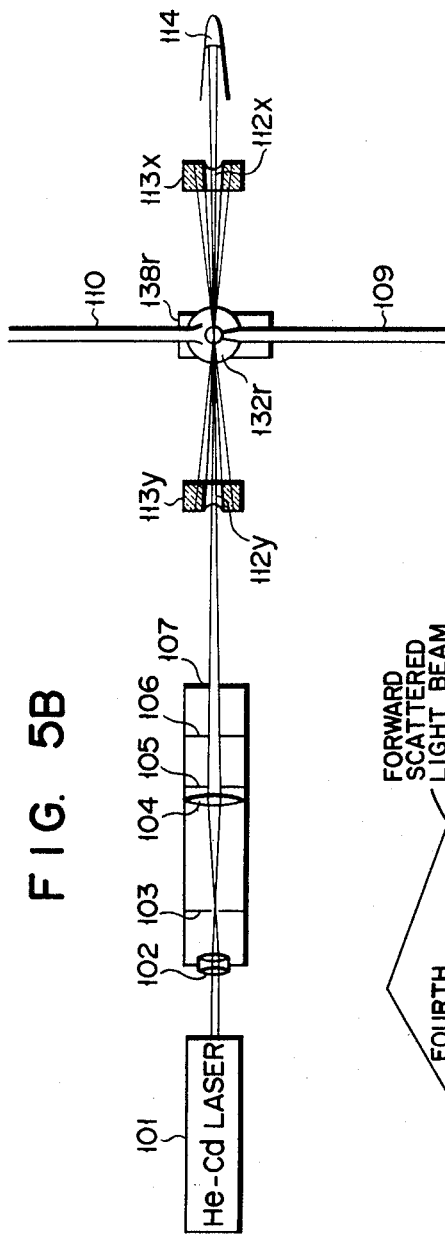
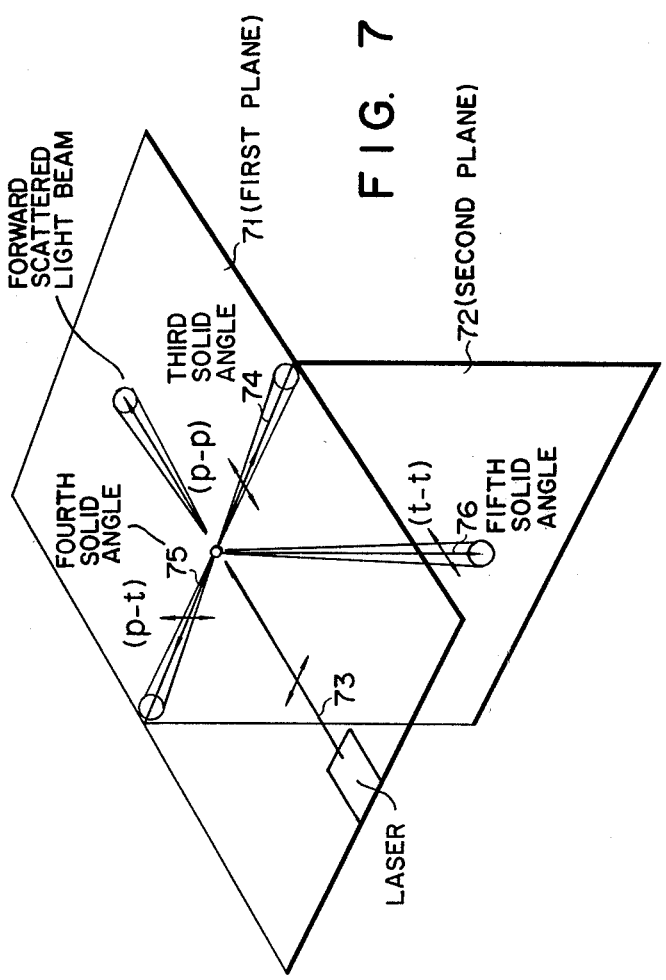

DUST PARTICLE ANALYZER

CROSS REFERENCE TO THE RELATED APPLICATION

This is a continuation-in-part application of U.S. patent application Ser. No. 726,030 filed on Sept. 23, 1976, now abandoned.

BACKGROUND OF THE INVENTION

This invention generally relates to the technology of analyzing the nature of dust particles contained in the environmental air by observing light beams scattered from the dust particles.

Said analysis primarily consists in giving information on the nature of the atmospheric dust particles, namely, the various forms thereof such as fibrous, mineral, liquid, bacterial, etc., on the size of said dust particles and the frequency at which said dust particles appear in the air.

The principle of analyzing dust particles by light beams scattered therefrom is based on the fact that light beams scattered from dust particles essentially include information on the size, refractive index and shape of said dust particles. The object of this invention is to meet a strong demand for further improvement of the dust particle-analyzing technology by engineering for control of air pollution as well as for cleaning air present in the industrial zone and hospitals.

This invention relates particularly to the application of a laser as a light source for the observation of scattered light. Recent development in the ultraviolet and shorter visible wave gas laser has an important implication in rendering the new development involved in this invention available for practical use.

Three types of commercially available dust counters were described by W. R. Zinky (J. Air Pollution Control Assoc. 12, 578 (1962), J. M. Raudall and J. D. Keller (Am. Ind. Hyg. Assoc. J. 29, 257 (1968)) and D. Scinclair (J. Air Pollution Control Assoc. 17, 105 (1967)) respectively. These instrument differ from each other mostly in the geometry of illuminating and observing optical systems. The first one uses an observing optical system having its axis disposed perpendicular to that of the illuminating optical system. The second one contains an observing optical system receiving a forward hollow cone of a desired solid angle coaxial with that which is emitted from the illuminating optical system. All these three instruments are alike in applying white light as a source of illumination and in employing an observing optical system having a large solid angle.

According to the theory of light scattering by a spherical dielectric particle proposed by G. Von Mie (Annalev d. Physik, 25, 378 (1908)), the scattering cross-section S, that is, the scattered light intensity per unit solid angle of observation per unit intensity of the illuminating light shows a complicated dependence on the solid conical angle as a function of the refractive index n and the reduced dust particle diameter $\delta$ especially for larger values of $\delta$ than 2. The reduced dust particle diameter $\delta$ is defined as:

$$\delta = 2\pi a/\lambda \tag{1}$$

where $2a$ and $\lambda$ denote the diameter of the dust particle and the wavelength of the illuminating light respectively. The scattering cross-section S shows a rather smooth dependence on $2a$ and is relatively insensitive to n as averaged over the wavelength $\lambda$ of the white light source and over the solid angle of observation. Various light scattering dust counters proposed to date which use white light and contain an observing optical system for receiving a forward hollow cone of a large solid angle in view of the above-mentioned facts, as well as the aforesaid three instruments claim the good light-collecting efficiency of the observing optical system and the reliable deduction of the particle diameter $2a$ even when an operator lacks the knowledge of the refractive index n of the dust particle.

A light scattering apparatus using a He-Ne laser having a wavelength of 633 nm as an illuminating source and using a forward hollow cone of a slim solid angle for observation of dust particles was proposed by W. Kaye (analytical Chemistry 45, 221A, 1973).

When used for observation of the Debye-Zimm scattering from a liquid solution and Rayleigh scattering from dust particles dispersed in a liquid carrier, the apparatus proposed by W. Kaye demonstrated the favourable nature of a laser used as a light source for a aerosol light-scattering apparatus. The highly coherent nature of a laser attains a high luminosity in a light scattering space even by use of an illuminating optical system emitting a beam of light having an acute conical solid angle.

Further, the above-mentioned nature of a laser enables a sufficient amount of scattered light energy to be collected even in the slim solid angle region of a forward hollow cone received by the observing optical system, thereby attaining the observation of the substantially true forward light scattering just outside the cone emitted from the illuminating optical system without any harmful instrumental background light scattering which might occur in the absence of dust particles.

According to Mie's theory referred to above, the light-scattering cross-section S of a spherical dielectric particle for a small $\delta$ is given as:

$$S = (\lambda/2\pi)^2 (n^2-1)^2 (n^2+2)^{-2} \delta^6 \tag{2}$$

Equation (2) shows that the light-scattering cross-section S is proportional to $\lambda^{-4}$ and $(2a)^6$ for a small $\delta$. Accordingly, it is essential to use a light source having a shorter wavelength for the detection of dust particles of small diameters. This partly explains the reason why the prior dust counters have failed to obtain good results with respect to dust particles having a finer diameter than 0.3 micrometer.

SUMMARY OF THE INVENTION

It is accordingly the object of this invention to provide a dust particle analyzer giving information on the number, refractive index, and diameter of dust particles contained in a volume of sample air under surveillance.

This invention is based on the discovery that the diameter $2a$ and the refractive index n of a spherical particle can be determined separately by the simultaneous observation of the substantially true forward and backward scattering of light beams. To avoid unnecessary complication, description is only given of the case where $\delta$ is small.

According to any theoretical inference from Mie's theory, the sum of square roots of the forward light-scattering cross section $S_o$ of a dust particle and the backward light-scattering cross section $S_\pi$ thereof and the difference between said square roots are given by:

$$u \propto So^{\frac{1}{2}} + S\pi^{\frac{1}{2}} = 2\left(\frac{\lambda}{2\pi}\right) \frac{2^2 - 1}{n^2 + 2} \delta^3 \qquad (3)$$

and $$v \propto So^{\frac{1}{2}} - S\pi^{\frac{1}{2}} = 2\left(\frac{\lambda}{2\pi}\right) \frac{1}{30} \frac{(n^2 - 1)(2n^2 + 3)}{2n^2 + 3} \delta^5 \qquad (4)$$

According to this invention, n and δ can be determined easily from two observed values u and v given in Equations (3) and (4).

The values of u and v which are more complicated functions in the case of a large δ, can be determined in advance by a theoretical calculation. Therefore it is possible to deduce n and δ directly with the aid of either a graphical or computational method.

Another feature of this invention is to provide two practical methods for determining n and δ from u and v given in Equations (3) and (4). One method consists in the simultaneous observation of signals x and y representing light beams scattered forward and backward from dust particles.

The signals x and y, which are proportional to So and Sπ respectively, are converted into digital signals. Functions u and v, which are the sum of, and the difference between, $x^{\frac{1}{2}}$ and $y^{\frac{1}{2}}$ respectively, are calculated by means of an automatic calculator. Then, the occurrence of the scattered light signal is registered in the memory of the calculator whose addresses are designated by (u,v). The results obtained represent the distribution of the nature of the dust particles characterized by u and v. If necessary, the distribution is converted into the form denoted by n and δ. The other method consists in calculating the values of w=v/u and u by means of analog operational amplifiers from x and y. The signals v and u are supplied to the vertical and horizontal input terminals of a cathode-ray oscilloscope. The slope of the resulting display on the CRT indicates the value of w. Thus, each occurrence of dust particles causes a trace to be dashed off on the oscilloscope display. The distribution of the dust particle as a function of n and δ is given by the number of end points in each block defined by constant-n and constant-δ curves.

This invention is based on another discovery that the depolarized component of light beams scattered from a dust particle in a direction of observation perpendicular to that of illumination has a considerable intensity except for liquid droplets, for instance, of acid mist or oil mist. This depolarized component of the scattered light is found to be a good measure of the asphericity of a dust particle, and consequently is used in this invention as a signal for defining the shape of dust particles.

According to another feature of this invention, two additional intensities of scattered light are observed in a direction perpendicular to that of illumination. With one of said scattered light intensities, both the illuminating light and the observed light are polarized in the plane of observation. With the other of said scattered light intensities, both the illuminating light and the observed light are polarized perpendicular to the plane of observation. A third function Z, which is the ratio of the square roots of these two scattered light intensities, is used as a supplement for more reliable determination of n and δ. For a small δ, Z is given as:

$$Z = \frac{\left(S\frac{\pi}{2}\right)^{\frac{1}{2}}_{t,t}}{\left(S\frac{\pi}{2}\right)^{\frac{1}{2}}_{p,p}} \simeq \frac{1}{15} \frac{(n^2 + 2)(n^2 - 1)}{(2n^2 + 3)} \delta^2 \qquad (5)$$

The former and latter suffixes to (Sπ/2) denote the direction of polarization of the illuminated light and that of the observed light relative to the plane of observation. The letter "p" indicates the in-plane polarization and the letter "t" shows the perpendicular polarization.

The recently available He-Cd laser has an important significance in rendering this invention pratically available.

Application of a He-Cd laser having 442 nm and 325 nm wavelengths as a light source for the observation of scattered light beams attains the observation of the substantially true forward and backward scattering of light beams even in the slim solid angle region of a hollow cone of a light beam received by the observing optical system.

In conclusion, this invention presents a dust particle analyzer giving information on the refractive index, shape and size of a dust particle under surveillance, providing a remarkable improvement in the technology of analyzing dust particles.

BRIEF DESCRIPTION OF THE DRAWING

Further and more specific objects and advantages of this invention are made apparent in the following detailed description of preferred embodiments thereof when they are considered in conjunction with the accompanying drawings, in which:

FIG. 1 is a schematic representation of a basic configuration of this invention employing signals denoting light beams which are designated as x and y and are scattered forward and backward, respectively, from dust particles.

FIG. 3A is a schematic block circuit diagram of an analog data-processing apparatus according to a second embodiment of the invention for determining n and δ from x and y: FIG. 3B is an arithmetic analog circuit representing the parts of the operational amplifiers 129 and 130 in FIG. 3A;

FIG. 5 schematically presents a first modification of the invention employing the signals denoting forward, backward, perpendicular p-p polarized and perpendicular p-t polarized light beams, which are designated as x, y, p and r respectively:

FIG. 5B is a side elevational view in partial cross-section;

FIG. 6 is a schematic representation of a second modification of the invention employing the signals denoting forward, backward, perpendicular p-p polarized, perpendicular p-t polarized and perpendicular t-t polarized scattered light beams which are designated as x, y, p, r and t respectively:

FIG. 7 schematically shows the directions in which the illuminated light beams and the scattered light beams are polarized relative to the plane of observation.

DETAILED DESCRIPTION OF THE PREFERRED EMBODIMENTS

Figure 1A:
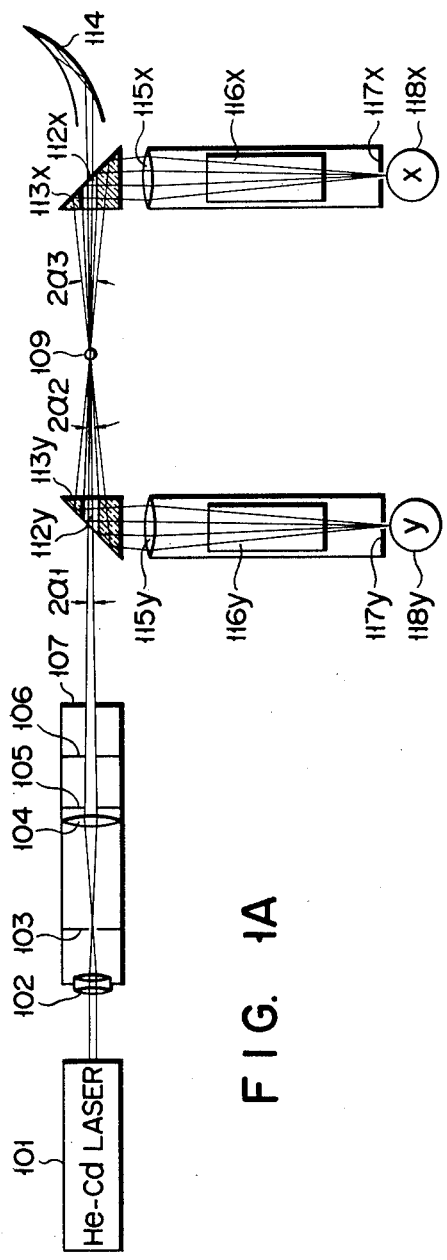
FIG. 1A is a plan view in partial cross-section.
Figure 1B:
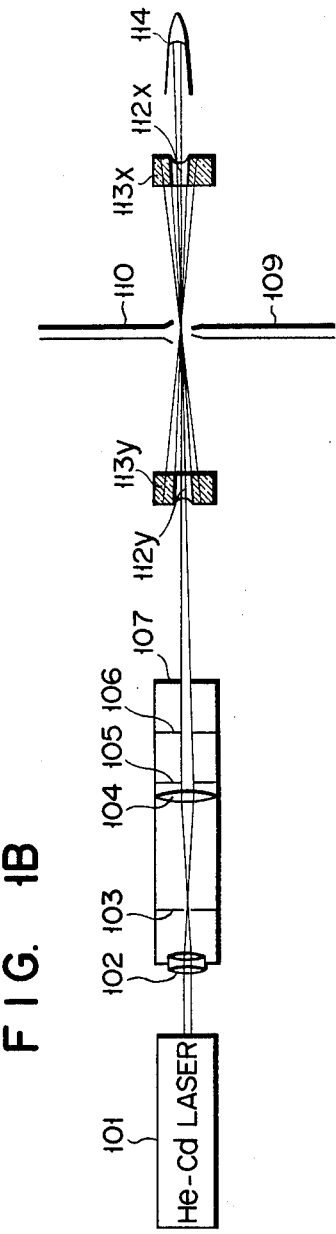
FIG. 1B is a side elevational view in partial cross-section.

Referring to FIGS. 1A and 1B, referential numeral 101 is a He-Cd laser producing a light beam having output power Po of 10 mW and a wavelength $\delta$ of 442 nm and polarized in the plane of FIG. 1A. A light beam of 1.8 mm diameter emitted from the He-Cd laser 101 is focussed on a circular slit 103 by a set of lenses 102. The circular slit 103 having a diameter of 0.1 mm serves to remove the fringing part of the angularly distributed light beam. In this case, substantial precaution is taken to prevent light energy from being placed in the lowest Gaussian mode of the light beam emitted. A lens 104 having a local length of 36 mm and diameter of 10 mm focuses divergent light beams passing from the circular slit 103 to the center of a light-scattering space in the form of a conical beam with a small angle $\alpha_1$ of 0.005 radian. Circular field-stops 105, 106 and 107 having diameters of 4 mm, 3.5 mm and 3 mm respectively, remove the undesirable fringing part of the field distribution of the light beam emitted. In this case, precaution is taken substantially to prevent light energy from being placed in the lowest Gaussian mode of the light beam supplied.

The circular field-stops 105, 106 and 107 also prevent the unnecessary scattering of light beams from the circular slit 103 and the lens 102 from forming the background illumination of the light-scattering space.

The size D of a diffraction-limited spot as determined in terms of $1/e^2$ power point and the focal depth L at the apex of Gaussian cone beam are respectively expressed as follows:

$$D = (4/\pi)\lambda/\alpha_1 \qquad (6)$$

and $$L = (4/\pi)\lambda/\alpha_1^2 \qquad (7)$$

The intensity of illumination at the focus (the apex of the conical light beam) Io is given by $$Io = (\pi/2)Po\alpha_1^2/\lambda^2 \qquad (8)$$

Figure 1C:
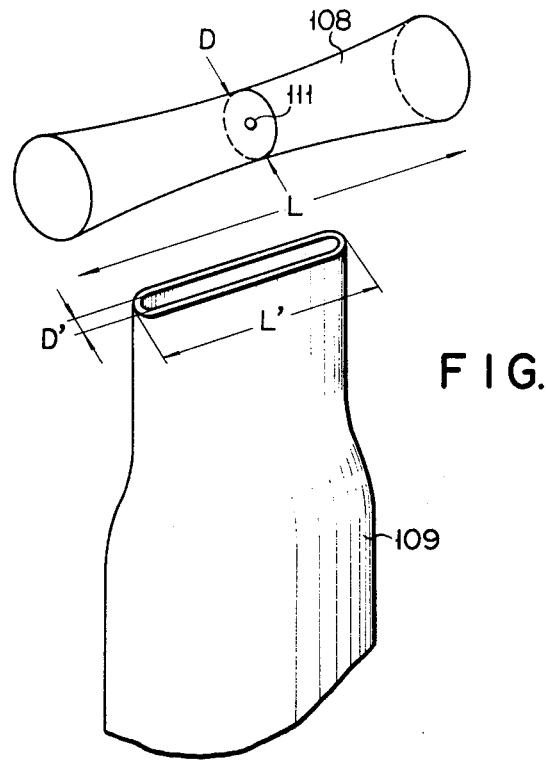
FIG. 1C is an enlarged view in perspective of a nozzle through which sample air is introduced.

That is, a highly illuminated region 108 (FIG. 1C) 112 $\mu$m in diameter, 22.5 mm in length and measuring 2.01 w/m² at the center of the scattering space is produced as shown in FIG. 1C. A nozzle 109 through which a volume of sample air is conveyed to the highly illuminated region 108 and a suction pipe 110 (FIG. 1B) which collects said volume of sample air are placed perpendicular to the axis of the illuminating conical light beam. Referring to FIG. 1C, the aperture of the nozzle 109 has a length L' and a width D' with its lateral side disposed parallel to the axis of the illuminating conical light beam. Provided L' and D' are respectively chosen to be smaller than about half the measurement L and D, denoting the length and width of the highly illuminated region 108, the intensity of a signal denoting light beams scattered from a dust particle in a homogeneous air flow passing through the nozzle aperture always falls within 60% of the maximum value of the intensity of a signal denoting light beams scattered from the dust particle 111 passing through the center of the highly illuminated region 108. In this embodiment, L' and D' are 10 mm and 0.05 mm respectively.

A 45° prism 113x having a conical bore 112x is so positioned that the cone of the bore 112x is coaxial and coapical with that of the illuminating conical light beam. The cone of the bore 112x has an angle $\alpha_2$ of 0.01 radian which is larger than $\alpha_1$ and fully allows the passage of the illuminating Gaussian light beam.

The 45° prism 113x collects light beams scattered from a dust particle 111 passing through the highly illminated region at a solid angle defined by an outer cone having an angle of $\alpha_3$ and a coaxial and coapical form with the illuminating conical light beam and the conical form of the bore 112x. A Rayleigh horn 114 traps a conical light beam passing through the bore 112x. The angle $\alpha_3$ has its value so chosen as to make the value of cos $(\alpha_3/2)$ substantially equal to unity and consequently enable the collected scattered light substantially to represent forward scattered light. Namely, said angle $\alpha_3$ is chosen to be 0.1 radian in this embodiment. Thus, the solid angle of an observing conical light beam expressed by the following equation $$\Omega = (\pi/4)(\alpha_3^2 - \alpha_2^2) \qquad (9)$$

has a magnitude of $7.78 \times 10^{-3}$ steradian. A lens 115x having a focal length of 40 mm and diameter of 20 mm focusses an image of the highly illuminated region on a circular slit 117x having a diameter of 0.1 mm. Accordingly, light beams scattered forward from a dust particle at an observation solid angle given in Equation (9) pass through the circular slit 117x and are concentrated on a photo-multiplier tube 118x. A Glan-Thompson prism 116x selects the scattered light beams polarized in the plane of FIG. 1A. A signal current x denoting light beams scattered forward from a dust particle which is supplied from the photo-multiplier tube 118x having a quantum efficiency $\eta$ and a diode gain G is expressed as follows:

$$x = \eta G(\lambda q/hc) Io \, So \, \Omega \qquad (10x)$$

wherein h, c and q represent Plank's constant, light velocity, and electronic charge respectively. With the values of $\eta$ and G set at 0.25 and $6 \times 10^6$, and an approximate expression of Equation (2) adopted for a small $\delta$, then the signal current x representing light beams scattered forward from a dust particle having $n^2$ of 2 and $\delta$ of 0.1 $\mu$m is $3.35 \times 10^{-7}$ ampere. The magnitude of a minimum detectable photo-current signal is given by $$xn = (2q \, B \, F \, G \, Id)^{\frac{1}{2}} \qquad (11)$$

wherein Id and F are the anode dark current and the noise figure of the photo-multiplier tube 118x, and B is the band width of an amplifier disposed immediately after the detector. B is so chosen as to prevent the deterioration of a pulsed photo-current response delivered by a dust particle passing through the highly illuminated region of the light-scattering space. With Id, F and B chosen to have values of $10^{-9}$ ampere, 3 and $10^4$ hertz respectively, then xn is calculated to be $7.6 \times 10^{-9}$ ampere. A signal current denoting light beams scattered forward from a dust particle ($n^2 = 2$ and $\delta = 0.1$) is sufficiently larger than the above-mentioned amperage.

A 45° prism 113y is made similar to the 45° prism 113x and is positioned symmetrical therewith relative to a plane perpendicular to the axis of the illuminating conical light beam and extending through the apex of the conical light beam. The 45° prism 113y collects light beams scattered backward at an observation solid angle, the magnitude of which is given in Equation (9). A lens 115y, Glan-Thompson prism 116y, circular slit 117y and photo-multiplier tube 118y are manufactured and positioned in the same manner as the lens 115x, Glan-Thompson prism 116x, circular slit 117x and photo-multiplier tube 118x respectively, excepting that the former group of elements deal with the backward scattered light beams. The photo-multiplier tube 118y generates a signal current y denoting backward scattered light beams, said current being expressed as follows:

$$y = \eta G(\lambda q/hc) I_o S\pi \Omega \qquad (10y)$$

Thus, the cross-sections $S_o$ and $S_\pi$ of a dust particle scattering light beams forward and backward are obtained from Equations (10x) and (10y). Accordingly, the refractive index n and reduced diameter δ of a dust particle passing through the highly illuminated region 108 can be determined from Equations (2) and (3). There will now be described by reference to FIG. 2 a digital data processing apparatus according to the first embodiment of this invention for determining n and δ from x and y.

Preamplifiers 119x, 119y having a bandwidth of 100 megahertz units provide counting pulses for counters 120x, 120y from a single-photon response appearing in the output of the photo-multipliers 118x, 118y contained in a pulsed photo-current response delivered by a dust particle passing through the highly illuminated region 108 of the scattered space. Counters 120x, 120y, each having 14 bits, start to count upon being triggered by start-signals from trigger pulse generators 121x, 121y, which distinguish a bunch of single photon responses from a discretely occurring noise pulse output from the photo-multiplier tubes 118x, 118y respectively. The number of pulses in the bunch of single photon responses is proportional to the intensity of signal current derived from light beams scattered from a dust particle.

Figure 2:
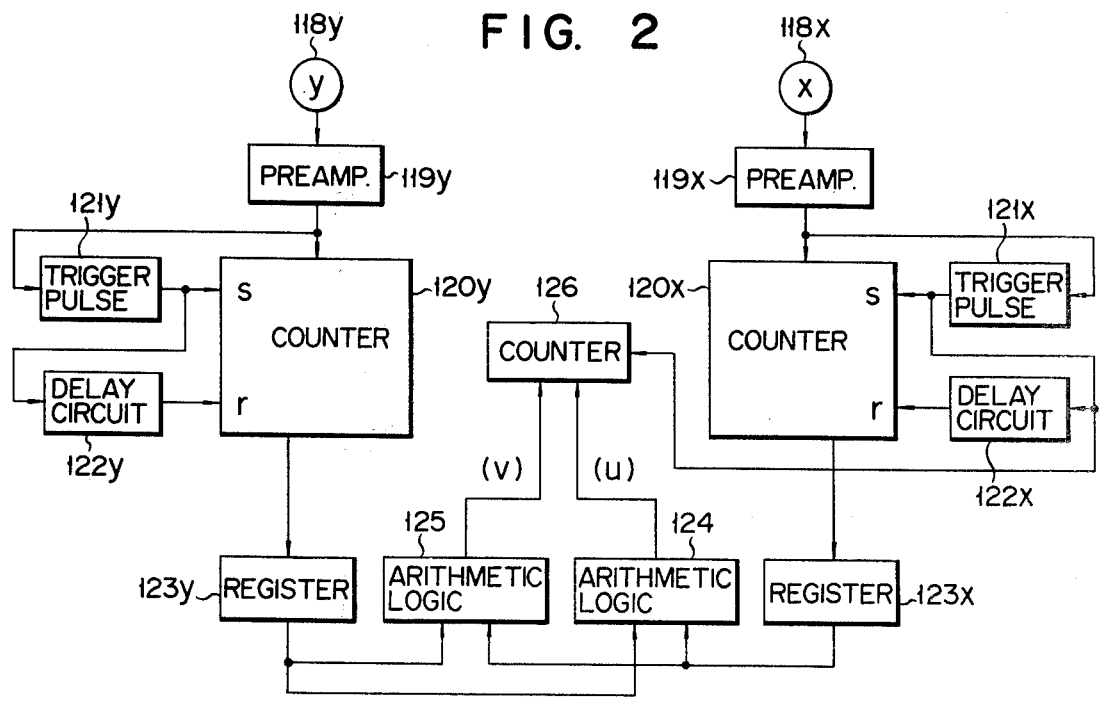
FIG. 2 is a schematic block circuit diagram of a digital data processing apparatus according to a first embodiment of this invention for determining n and δ from x and y of this invention.

Referring to FIG. 2, trigger pulse generators 121x, 121y generate start signals when output signals from preamplifiers 119x, 119y have a higher voltage than a threshold level. Counters 120x, 120y stop counting when triggered by stop-signals from delay circuits 122x, 122y providing a delay time of 100 μs corresponding to the longest transit time required for a dust particle to pass through the highly illuminated region 108 of the scattering space. The counters 120x, 120y transfer counted digits to registers 123x, 123y, each consisting of 14 bits, just after the stoppage of counting.

Accordingly, signal current x derived from light beams scattered forward from a dust particle and the signal current y obtained from light beams scattered backward from a dust particle which are already converted into digital signals are transferred to the registers 123x, 123y respectively. At this time the counters 120x, 120y are reset to be ready to receive the succeeding photo-current response delivered from another dust particle.

Arithmetic logic circuits 124 and 125 calculate quantities $v = S_o^{\frac{1}{2}} - S_\pi^{\frac{1}{2}}$ and $u = S_o^{\frac{1}{2}} + S_\pi^{\frac{1}{2}}$ respectively from outputs from the x—signal register 123x and y—signal register 123y. A multi-addressed counter 126, the addresses of which are specified by the quantities u and v, counts start signals delivered from the trigger pulse generator 121x. Thus, after a certain time interval, counted numbers stored in the addresses specified by the quantities u and v represent the number of those dust particles having n and δ corresponding to the specific values of said u and v which have passed through the highly illuminated region 108 of the scattering space during the above-mentioned time interval.

There will now be described with reference to FIG. 3A an analog data-processing apparatus according to the second embodiment of this invention for determining n and δ from x and y.

Preamplifiers 127x, 127y have a bandwidth of 15 kilohertz corresponding to the average transit time required for a dust particle to pass through the highly illuminated region 108 of the scattering space. The output signal currents x and y from the photo-multiplier tubes 118x, 118y are amplified by the preamplifiers 127x, 127y respectively. Operational amplifiers 128x, 128y give output signals X and Y proportional to $S_o^{\frac{1}{2}}$ and $S_\pi^{\frac{1}{2}}$, respectively. An operational amplifier 129 gives an output signal u equal to the sum of two input signals, X and Y, namely, $$u = S_o^{\frac{1}{2}} + S_\pi^{\frac{1}{2}} \qquad (12)$$

An operational amplifier 130 gives an output signal V equal to the difference between the two input signals X and Y, namely, $$v = S_o^{\frac{1}{2}} - S_\pi^{\frac{1}{2}} \qquad (12')$$

Figure 4:
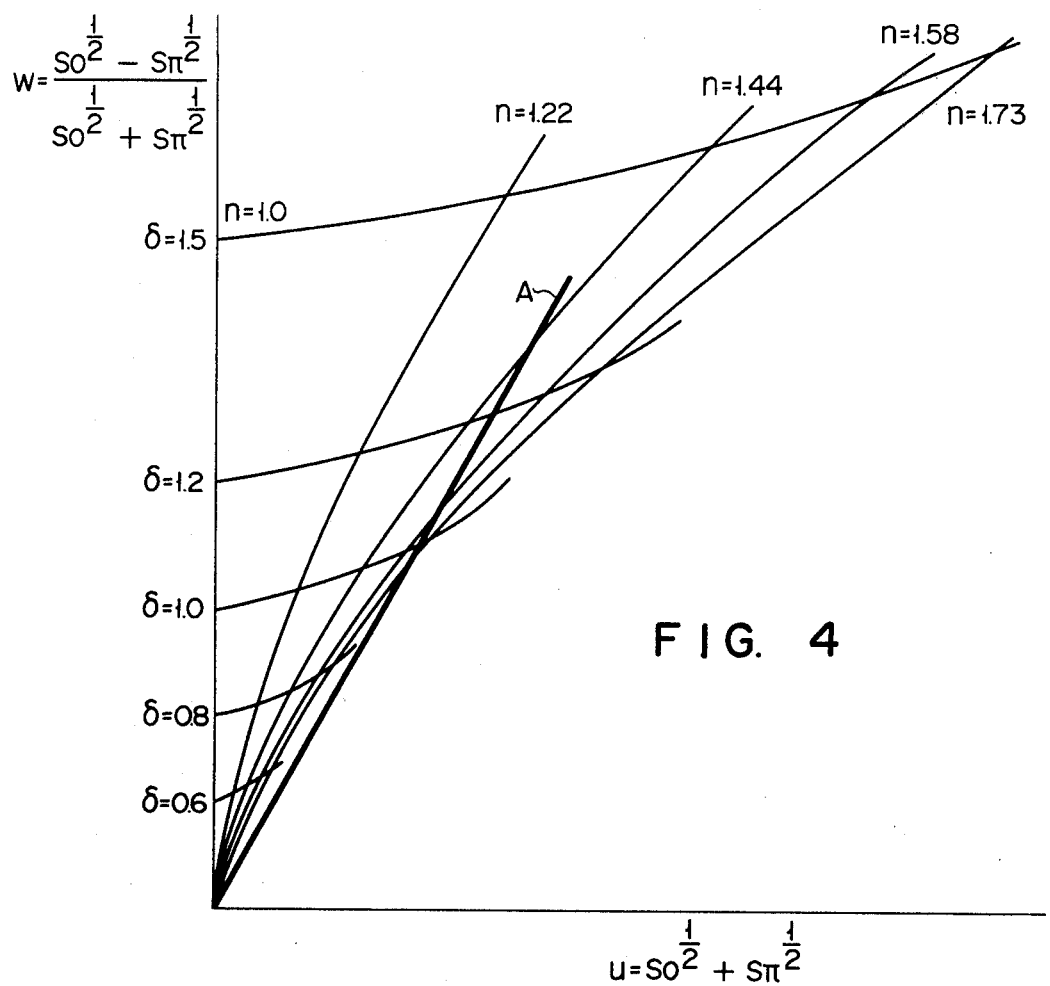
FIG. 4 is a graphic representation of the traces of signals denoting scattered light beams appearing on a cathode-ray oscilloscope and the curves of constant n and constant δ used in defining the distribution of dust particles according to n and δ as obtained from said second embodiment.

Therefore, the ratio w of the signal v to the signal u, $$w = (S_o^{\frac{1}{2}} - S_\pi^{\frac{1}{2}})/(S_o^{\frac{1}{2}} + S_\pi^{\frac{1}{2}}) \qquad (13)$$

is obtained to compensate the nonuniformity in intensity of the illuminating conical light beam. The output signals u, v from the operational amplifiers 129 and 130 are supplied to the horizontal and vertical input terminals of a cathode-ray oscilloscope 131 respectively. The parts of the operational amplifiers 129 and 130 consist of an arithmetic analog circuit as represented in FIG. 3B. When the signals u and v are supplied to the horizontal and vertical terminals of the cathode-ray oscilloscope 131, respectively, a trace showing the relation between the ratio w and the signal u shown in FIG. 4 can be obtained on the display surface of the cathode-ray oscilloscope 131. A well-known cathode-ray oscilloscope can be used as the oscilloscope 131 and a further explanation thereof may be omitted. Thus, a pulsed signal denoting light beams scattered from a dust particle passing through the highly illuminated region 108 of the light-scattering space causes a trace to be dashed off on the cathode-ray oscilloscope 131. The vertical and horizontal components of the trace are proportional to w and u respectively as shown in FIG. 4.

There will now be described by reference to FIG. 4 a graphic record obtained on the cathode-ray oscilloscope 131.

A heavy line A shows a trace corresponding to a dust particle having n of 1.41 and δ of 1.35. Sharply rising curves denote those of the constant n when the dust particle has values of 1.0, 1.22, 1.44, 1.58 and 1.73, respectively. Slowly rising curves represent those of the constant δ when dust particle has values of 1.5, 1.2, 1.0, 0.8 and 0.6, respectively. The parameters n and δ corresponding to the end point of the trace of the dust particle which produced a pulsed signal denoting light beams scattered forward or backward therefrom indicate the refractive index and diameter of said dust particle. The photographic record of FIG. 4 obtained on the cathode-ray oscilloscope 131 during a certain time interval presents the traces of many dust particles. Statistical data on the numbers of the end points of the traces of dust particles included in the respective regions defined by constant n and constant δ curves gives the distribution of the refractive index and diameter of the dust particles contained in the sample air determined in the above-mentioned time interval.

There will now be described by reference to FIGS. 5 and 7 a first modification of this invention which employs in a first plane 71 shown in FIG. 7 a forward, a backward, a perpendicular p-p polarized and a perpendicular p-t polarized signals denoting light beams scattered from a dust particle. The parts of FIG. 5 denoted by the same numerals as in FIG. 1 are manufactured and positioned in the same manner as those used in FIG. 1 and are intended to serve the same purpose.

Figure 5A:
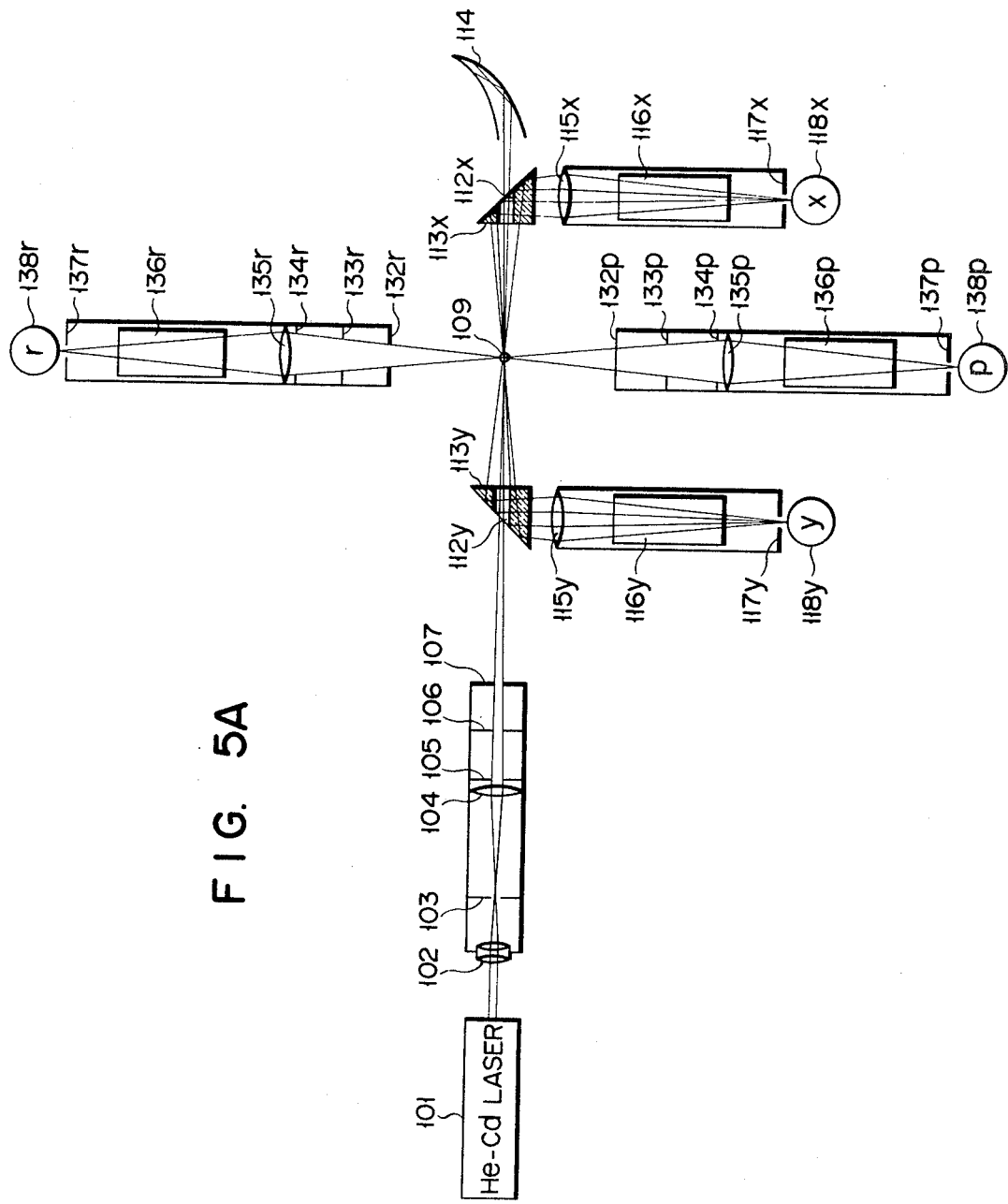
FIG. 5A is a plan view in partial cross-section.

Circular stops 132p, 133p, 134p collect light beams 74 scattered sidewise from a dust particle passing through the highly illuminated region 108 at the solid angle of a cone, the axis of which lies in the plane of FIG. 5A, that is, a first plane 71 of observation, and is perpendicular to the axis of the illuminating conical light beam 73. The cone has an angle equal to $\alpha_3$ which is so small that the collected scattered light beam is substantially perpendicular to the illuminating beam 73. In this case the magnitude of the solid angle $\Omega'$ of an observing conical light beam is given by $$\Omega' = (\pi/4)\alpha_3^2 \tag{9'}$$

which is substantially equal to that given by Equation (9). A lens 135p focusses the image of the highly illuminated region on an oblong slit 137p. Accordingly, an observing conical light beam 74 having a solid angle indicated by Equation (9') and scattered from a dust particle in a perpendicular direction to an illuminating conical light beam 73 passes through the oblong slit 137p and falls on a photo-multiplier tube 138p. A Glan-Thompson prism 136p selects the scattered observing light beam 134 polarized in the first plane 71 of observation. An output signal current p from the photo-multiplier tube 138p denoting the perpendicular p-p polarized scattered light is given by $$p = \eta G \left( \frac{\lambda q}{hc} \right) I_0 \left( S \frac{\pi}{2} \right)_{p,p} \Omega' \tag{10p}$$

Each of the circular field-stops 132r, 133r, 134r, lens 135r, oblong slit 137r and photo-multiplier tube 138r are manufactured and positioned in the same manner and serve the same object as the circular field-stops 132p, 133p, 134p, lens 135p, oblong slit 137p and photo-multiplier tube 138p respectively, excepting that the cone having an observing solid angle is positioned just opposite to that of an observing optical system composed of elements 132p, 133p, 134p, 135p, 137p, and 138p. A Glan-Thompson prism 136r selects the scattered light beam 75 polarized perpendicular to the plane 71 of observation. An output signal current r from the photo-multiplier tube 138r denoting the perpendicular p-t polarized scattered light beam is given by $$r = \eta G \left( \frac{\lambda q}{hc} \right) I_0 \left( S \frac{\pi}{2} \right)_{p,t} \Omega' \tag{10r}$$

The ratio d where $$d = r/p \tag{11}$$

is a measure of the depolarization caused by the asphericity of a dust particle under serveillance. Accordingly, a signal expressed by Equation (11) is used in determining the shape of a dust particle.

There will now be described by reference to FIGS. 6 and 7 a second modification of this invention which employs signals denoting forward, backward, perpendicular p-p polarized and perpendicular p-t polarized scattered light beams in the first plane 71 of FIG. 7 and a signal denoting a perpendicular t-t polarized scattered light beam in the second plane 72 of FIG. 7.

Figure 6B:
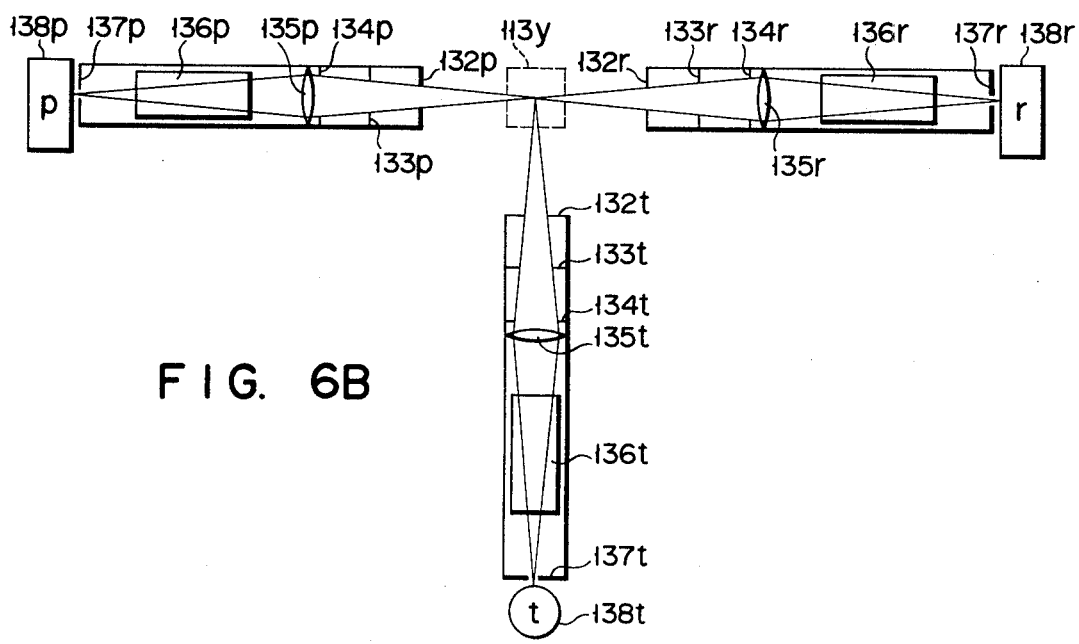
FIG. 6B is an end view as though one were looking backwardly toward the laser.
Figure 6A:
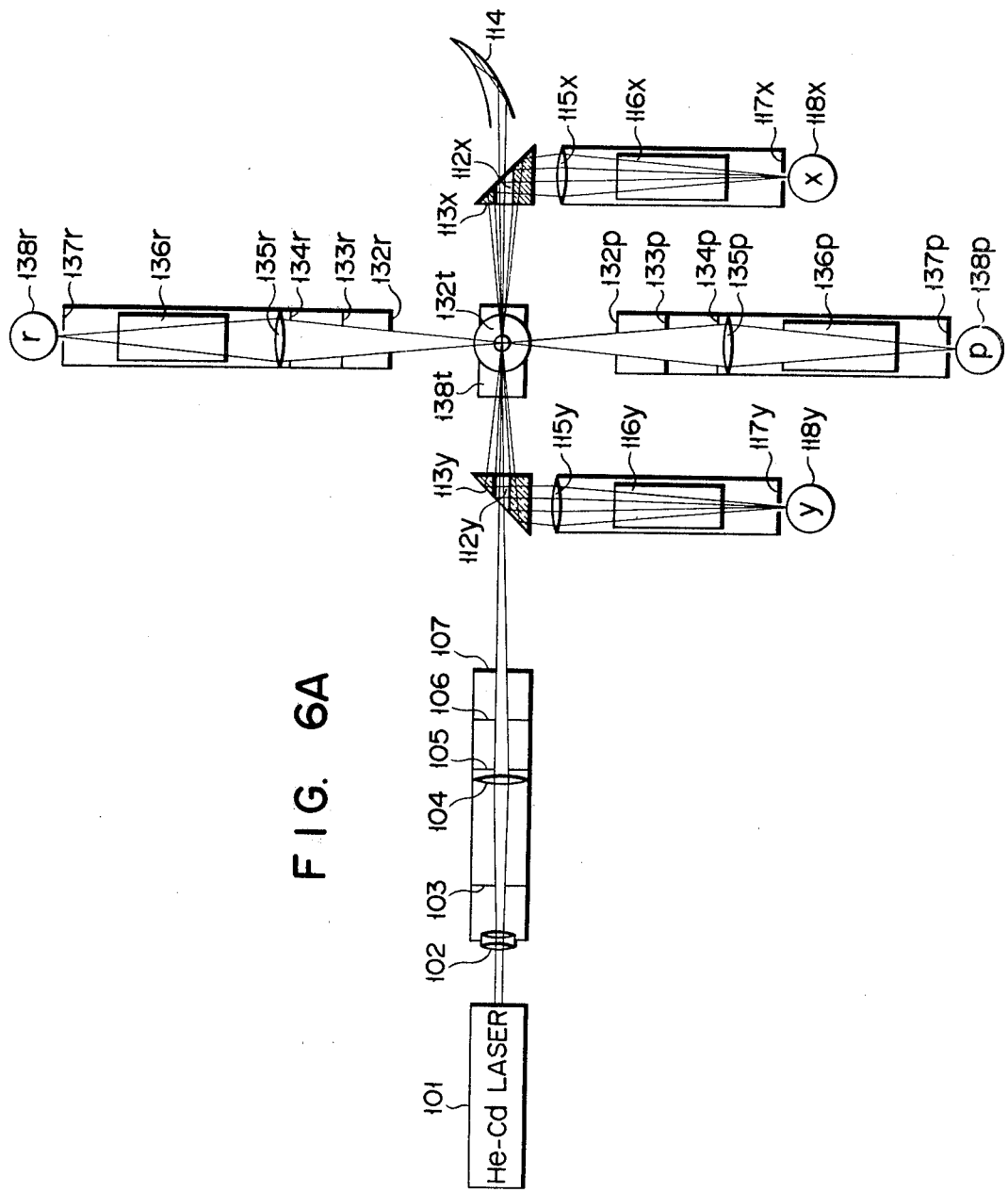
FIG. 6A is a plan view in partial cross-section.

The parts of FIG. 6 denoted by the same numerals as those of FIG. 5 are manufactured and positioned in the same manner and serve the same object as in FIG. 5. Circular field stops 132t, 133t and 134t collect an observing conical light beam 76 scattered from a dust particle passing through the highly illuminated region 108 at a solid angle defined by a cone, the axis of which lies in the plane of FIG. 6B, that is, the second plane 72 of observation, and is perpendicular to the axis of the illuminating conical light beam 73. In this case, therefore, the second plane 72 of observation is perpendicular to the first plane 71, namely, the direction in which the illuminating conical light beam 73 is polarized is perpendicular to the second plane 72 of observation. The cone of an observing light beam has an angle equal to $\alpha_3$ which is so small that the collected scattered light is substantially perpendicular to the illuminating beam 73. In this case the magnitude of the solid angle of an observing conical light beam is equal to $\Omega'$ given in Equation (9'). A lens 135t focusses the image of the highly illuminated region on an oblong slit 137t. Accordingly, an observing conical light beam 76 scattered from a dust particle in a perpendicular direction to an illuminating light beam at an observing solid angle, the magnitude of which is given by Equation (9') passes through the oblong slit 137t and falls on a photo-multiplier tube 138t. A Glan-Thompson prism 136t selects the observed scattered light beam 76 polarized in the second plane 72 of observation. An output signal current t from the photo-multiplier tube 138t denoting the perpendicular t-t polarized scattered light beam is given by $$t = \eta G \left( \frac{\lambda q}{hc} \right) I_0 \left( S \frac{\pi}{2} \right)_{t,t} \Omega' \tag{10t}$$

The ratio e, where:

$$e = t/p \tag{12}$$

The above equation (12), 00, whose approximation for small δ is given by Equation (5), can be used to provide additional information on n and δ of a dust particle. That is, the reliability of the refractive index n and diameter δ given by Equations (2) and (3) can be checked by signals denoting the perpendicular p-p polarized scattered light beam and perpendicular t-t polarized scattered light beam. With the second modification, observation was made of forward, backward, perpendicular p-p polarized, perpendicular p-t polarized and perpendicular t-t polarized scattered light beams. However, this invention also includes the case, where observation is only made of forward, backward and t-t polarized scattered light beams. While, in the second embodiment, the cathode-ray oscilloscope 131 was used, it is possible to process the signals by a computer. Namely, the latter computer process consists in supplying output signals u, v from the operational amplifiers 129, 130 to the computer through an analog-digital converter, judging the magnitudes of said output signals u, v and adding 1 to the number of items of memory data classified by the magnitudes of the signals u, v, thereby easily determining the number of dust particles belonging to the respective groups defined by the magnitudes of the signals u, v.

What is claimed is:

1. A dust counter comprising:
   (a) a laser producing a light beam polarized in a first plane including said light beam;
   (b) means for converting said light beam into a Gaussian cone light beam of a first small angle at the cone apex;
   (c) means for conveying a volume of sample air containing dust particles under surveillance into a highly illuminated region at the waist of said Guassian cone light beam, said conveying means comprising a nozzle having an oblong aperture of a width corresponding to the waist diameter of said Gaussian cone light beam and of a length corresponding to said waist diameter divided by the apex angle of said cone light beam, with the length of the oblong aperture parallel to the axis of said cone light beam;
   (d) means for collecting forward scattered light from a dust particle under surveillance in a first solid angle larger than said first small angle and an outer cone of a third small angle, the cosine of which is substantially equal to unity;
   (e) means for collecting backward scattered light from said dust particle in a second solid angle surrounded by an inner cone of said second small angle and an outer cone of said third small angle;
   (f) means for collecting scattered light from said dust particle in a third solid angle, the center axis of which is perpendicular to that of said light beam and is in said first plane;
   (g) means for producing a first signal which is proportional to the component of said forward scattered light polarized in said first plane and scattered in said first solid angle
   (h) means for producing a second signal which is proportional to the component of said backward scattered light polarized in said first plane and scattered in said second solid angle;
   (i) means for producing a third signal which is proportional to the component of scattered light in said third solid angle which is polarized in said first plane;
   (j) means for obtaining a first parameter by calculating the sum of the first and second signals; for obtaining a second parameter by calculating the difference of the first and second signals; and for obtaining a ratio of said difference over said sum, wherein said parameters are known, mutually independent, functions of the refractive index and the diameter of said dust particle in the case where the shape of said dust particle is known to be spherical; and
   (k) means for counting the number of said dust particles in a volume of said sample air per each class which is classified according to said first and said second parameters.

2. The dust counter of claim 1, further comprising:
   (a) means for collecting scattered light from said dust particle in a fourth solid angle, the center axis of which is perpendicular to that of said light beam and is located in said first plane in opposed alignment with the center axis of said third solid angle; and,
   (b) means for producing a fourth signal which is proportional to the component of scattered light in said fourth solid angle which is polarized perpendicular to said first plane.

3. The dust counter of claim 2, further comprising:
   (a) means for collecting scattered light from said dust particle in a fifth solid angle, the center axis of which is perpendicular to that of said light beam and is in a second plane which is perpendicular to said first plane and including said light beam; and,
   (b) means for producing a fifth signal which is proportional to the component of scattered light in said fifth solid angle which is polarized perpendicular to said second plane.

4. The dust counter of claim 1, further comprising means for converting said first and said second signals into a first and a second digital signal, respectively.

5. The dust counter of claim 4 further comprising:
   (a) means for producing a fourth signal which is proportional to the scattered light intensity in a solid angle which is neither said first solid angle nor said second angle; and,
   (b) wherein said first and said second parameters are the ratio of said first signal over said fourth signal and the ratio of said second signal over said fourth signal, respectively.

6. The dust counter of claim 1 further comprising:
   (a) means for calculating a first and a second analog parameter from said first and said second signals, wherein said analog parameters are known, mutually independent functions of the refractive index and the diameter of said dust particle in the case where the shape of said dust particle is known to be spherical; and,
   (b) means for displaying a position defined by said first and said second analog parameters wherein a graphic record of said display in a certain time interval carries full information about the number of particles of which refractive index and of which diameter are contained in a volume of said sample air.

* * * * *